US009581546B2

(12) United States Patent
Schwarz et al.

(10) Patent No.: US 9,581,546 B2
(45) Date of Patent: Feb. 28, 2017

(54) APPARATUS AND METHOD OF INVESTIGATING COATINGS WITH EFFECT PIGMENTS (75) Inventors: Peter Schwarz, Koenigsdorf (DE); Uwe Sperling, Geretsried (DE)

(73) Assignee: BYK-GARDNER GMBH (DE)

( * ) Notice: Subject to any disclaimer, the term of this patent is extended or adjusted under 35 U.S.C. 154(b) by 819 days.

(21) Appl. No.: 13/538,284

(22) Filed: Jun. 29, 2012

(65) Prior Publication Data

US 2013/0027545 A1 Jan. 31, 2013

(30) Foreign Application Priority Data

Jul. 27, 2011 (DE) .................. 10 2011 108 599

(51) Int. Cl.
*H04N 7/18* (2006.01)
*G01N 21/47* (2006.01)
(Continued)

(52) U.S. Cl.
CPC ........... *G01N 21/474* (2013.01); *G01N 21/55* (2013.01); *G01N 21/8806* (2013.01); *G01N 2021/1765* (2013.01)

(58) Field of Classification Search
CPC ......... G01N 2021/1765; G01N 21/474; G01N 21/55; G01N 21/8806
(Continued)

(56) References Cited

U.S. PATENT DOCUMENTS 6,122,042 A * 9/2000 Wunderman ............ A61B 1/05
356/343
6,975,404 B2 12/2005 Schwarz ....................... 356/446
(Continued)

FOREIGN PATENT DOCUMENTS

DE   10122917      11/2002
DE   102004034160   2/2006
(Continued)

OTHER PUBLICATIONS

Lefcout, Alan, et al., Systematic approach for using hyperspectral imaging data to develop multispectral imagining systems: Detection of feces on apples, Science Direct, Computers and Electronics in Agriculture 54, pp. 22-35 (2006).*
European Search Report (w/English translation) issued in corresponding application No. 12153282.4, dated Nov. 6, 2012 (10 pgs).
First Office Action issued in corresponding Chinese Patent Appln. Serial No. 201210234723.9 dated Nov. 4, 2015, with English translation (9 pgs).
Japanese Office Action issued in application No. 2012-162890, dated Mar. 22, 2016 (8 pgs).

*Primary Examiner* — William C Vaughn, Jr.
*Assistant Examiner* — Naod Belai
(74) *Attorney, Agent, or Firm* — Hayes Soloway P.C.

(57) ABSTRACT

Radiation is irradiated by an irradiation device at a pre-set angle of incidence with respect to the surface onto the surface to be investigated, and the radiation scattered and/or reflected by this surface arrives at a radiation detector device arranged at a pre-set detection angle with respect to the surface and having an image-recording unit which records black-and-white images, wherein this radiation detector device permits a spatially resolved detection of the radiation reaching it. The irradiation device directs radiation in a first wavelength range onto the surface and the image-recording unit records a first spatially resolved image of this radiation scattered and/or reflected from the surface and the irradiation device directs radiation in a second wavelength range onto the surface and the image-recording unit records a second spatially resolved image of this radiation scattered and/or reflected from the surface.

19 Claims, 3 Drawing Sheets (51) Int. Cl.
*G01N 21/55* (2014.01)
*G01N 21/88* (2006.01)
*G01N 21/17* (2006.01)

(58) Field of Classification Search
USPC .......................................... 348/135, E7.085
See application file for complete search history.

(56) References Cited

U.S. PATENT DOCUMENTS

| | | | |
|---|---|---|---|
| 7,276,719 B2 | 10/2007 | Schwarz ................. | 250/559.36 |
| 7,626,709 B2 | 12/2009 | Schwarz et al. ............. | 356/600 |
| 7,714,997 B2* | 5/2010 | Shibata et al. ............. | 356/237.2 |
| 2004/0252308 A1 | 12/2004 | Prakash et al. ............. | 356/445 |
| 2005/0002038 A1 | 1/2005 | Sakaino et al. ............. | 356/446 |
| 2006/0033922 A1 | 2/2006 | Sperling et al. ............. | 356/446 |
| 2006/0092417 A1 | 5/2006 | Schwarz et al. ............. | 356/337 |
| 2007/0291993 A1* | 12/2007 | Nisper ................ | G01N 21/474 |
| | | | 382/108 |
| 2008/0094638 A1* | 4/2008 | Schwarz ........... | G01N 21/4738 |
| | | | 356/600 |
| 2008/0231865 A1 | 9/2008 | Schwarz et al. ............. | 356/601 |
| 2008/0297780 A1* | 12/2008 | Clasen ............... | G01N 21/8803 |
| | | | 356/237.2 |
| 2009/0086192 A1* | 4/2009 | He .......................... | G01J 1/124 |
| | | | 356/73 |
| 2013/0027545 A1* | 1/2013 | Schwarz .............. | G01N 21/474 |
| | | | 348/135 |

FOREIGN PATENT DOCUMENTS

| | | | |
|---|---|---|---|
| EP | 0773426 | 5/1997 | ............ G01B 11/24 |
| JP | H0949803 | 2/1997 | ............ G01B 11/24 |
| JP | 2000205846 | 7/2000 | |
| JP | 2002345760 | 12/2002 | ............... A61B 5/00 |
| JP | 2004354157 | 12/2004 | ............ G01N 21/01 |
| JP | 2006030203 | 2/2006 | ................ G01J 1/02 |
| JP | 2006030204 | 2/2006 | ................ G01J 3/46 |
| JP | 2008164628 | 7/2008 | ................ G01J 3/46 |
| JP | 2008268190 | 11/2008 | ............ G01B 11/28 |
| WO | WO2010103267 | 9/2010 | ............ A61B 5/103 |

\* cited by examiner

APPARATUS AND METHOD OF INVESTIGATING COATINGS WITH EFFECT PIGMENTS

BACKGROUND OF THE INVENTION

The present invention relates to an apparatus and a method of investigating surfaces, and in particular coatings. The invention is described with reference to so-called effect coatings, i.e. those coatings which have so-called effect pigments. Effect pigments of this type cause the coating in question to shine or sparkle or to assume a specific colour under specified conditions, for example with a light arriving at a specified angle.

In this case the most widely varying effect pigments and also the most widely varying optical properties thereof are known from the prior art. In this way, these effect pigments can have for example the most widely varying changes of colour.

Measurement instruments or apparatus are known from the prior art which are also used for the colour detection or optical detection of coatings of this type. In this case these apparatus usually have a plurality of light sources which direct specified light, for example standardized white light at different angles onto the respective surface provided with the coating. The radiation reflected by this surface is recorded by a camera, such as for example a CCD colour camera and the images are evaluated accordingly.

In this case, however, on account of the system there are limits to the accuracy of measurements of this type. Colour-image cameras of this type usually have an array with a plurality of photo detectors, in which case those detectors which are used to detect red light components, the detectors which are used to detect green light components and the detectors which are used to detect blue light components in each case are additionally arranged in any case at slightly different positions.

If coatings of this type with effect pigments are now recorded by a suitable appliance it is possible, in the event that an effect pigment reflects light in the red colour range for example, for this light to be reflected under specified measurements to those photocells which are intended to record blue or green light. In this case the corresponding photocells will display relatively low values or intensities and, in this way, the result is falsified.

In addition, in the case of illumination with a plurality of radiation sources of different spectral composition the separate illumination sources can be supplied with current individually. As a result, the brightness of this illumination can be adapted to the sample or the sensor characteristic for example in an optimum manner, and so a maximum measurement dynamic is achieved for each illumination.

The object of the present invention is therefore to provide an apparatus and a method which will permit a more accurate recording, or a less falsified recording, in particular of coatings with effect pigments.

SUMMARY OF THE INVENTION

In the case of a method according to the invention for the investigation of optical properties of surfaces, radiation is irradiated by an irradiation device at a pre-set angle of incidence with respect to the surface onto the surface to be investigated, and the radiation scattered and/or reflected by this surface or the radiation transmitted generally by this surface arrives (at least in part) at a radiation detector device arranged at a pre-set detection angle with respect to the surface and having an image-recording unit which records black-and-white images. In this case this radiation detector device permits a spatially resolved detection of the radiation encountering it. In general, instead of the camera which records black-and-white images, it is also possible for a camera to be used which has only one type of image-recording element in a plane at a right angle to the direction of light irradiation, this camera or each individual image-recording element of this camera being able both to supply information on the radiation intensity and to supply information on the irradiated wavelengths. This can be carried out by the pixels for the different colour components being arranged one behind the other in the irradiation direction.

According to the invention the irradiation device directs radiation in a first wavelength range onto the surface and the image-recording unit records a first spatially resolved image of these beams scattered and/or reflected from the surface, i.e. transmitted generally. In addition, the irradiation device directs radiation in a second wavelength range onto the surface and the image-recording unit records a second spatially resolved image of this radiation scattered and/or reflected from the surface. In this case the radiation in the first wavelength range and the radiation in the second wavelength range differ from each other at least in part and these radiations arrive staggered at least in part in terms of time at the surface. In this case, however, the radiation in the first wavelength range and the radiation. In the second wavelength range are irradiated at the same angle of incidence onto the surface. The spatially resolved image is to be understood in this case as being not only the actual image, but also a multiplicity of data (for example intensity values) from which this image can be assembled or derived.

Although it is therefore proposed according to the invention that a black-and-white camera or a greyscale camera (or a camera with only one specified type of pixel generally), which provides a higher spatial resolution, an improved linearity, an improved component reproducibility, greater measurement dynamics at the same time as a comparatively low component price, should be used for recording the images, nevertheless, in order to achieve an optical impression of the colour as well, it is proposed that the irradiation device should direct light of different colour onto the surface and so a multiplicity of images with different colour components should be recorded. On the basis of these images recorded in each case it is also possible for conclusions to be drawn in turn on the colour influences of the respective surface or even the effect pigments.

It is advantageous for the radiation scattered and/or reflected from the surface to be in general that radiation which is transmitted as a consequence of the radiation irradiated by the irradiation device, in particular transmitted to the image-recording device.

In this case it is possible for the individual effect pigments to be represented in an isolated manner by the formation of a threshold value in the overall image and for the characteristic optical properties of these effect pigments, such as for example colour, reflection behaviour, spatial scattering characteristics to be determined. In addition, such an isolated representation of the effect pigments by the formation of a threshold value in a histogram is possible.

This determination of the threshold value can be used both locally and in a brightness histogram. The threshold value can be used in this case as a fixed or as a dynamic value, which can be determined for example in a manner dependent upon the overall brightness of the image or an image contrast value.

In an advantageous method the mathematical formation of the threshold value is carried out in a fixed or a dynamic manner, and the formation of the threshold value is derived from image information such as image brightness or image contrast.

By calculating the flake characteristics of the different images with the different spectral illuminations, the optical properties of the effect pigments at the respective illumination angle can be determined as a result. What applies to the optical characterization of the effect flake, in particular, also applies to the surface as a whole.

In an advantageous method the irradiation of the surface with radiation in the first wavelength range and the irradiation with radiation in the second wavelength range are carried out staggered from each other completely in terms of time.

In a further advantageous method the wavelengths of the two irradiations which are directed onto the surface are also completely separate from each other. By way of example, green light is used in a first encounter and red light in a second encounter.

The image is therefore deliberately recorded with a black-and-white camera, since this has a higher resolution and no errors arise from different RGB detector units of the camera. It would also be possible to use a colour camera and to aggregate the figures of the respective sensor components.

It is advantageous for the image-recording unit to be an image-recording unit which has a plurality of identical photo-elements, i.e. In particular only one specific type of photo-elements and which is therefore suitable only for recording black-and-white or greyscale images.

It is preferable for the individual dark phase or the sensitivity or the linearity, which were determined for example by a preliminary calibration, to be taken into consideration mathematically in terms of pixels at each image recording. In this way, component tolerances, which can even occur between individual pixels, or other artefacts are compensated. Unlike using a colour-image camera, the differences between the individual colour pixels need not be taken into consideration here, and information need not be separated according to colour pixels.

In a further advantageous method the first image recorded by the image-recording unit and the second image recorded by the image-recording unit are compared with each other or are calculated with each other. Expressed more precisely, it is advantageous for the (intensity) values characteristic of the respective images to be compared with one another. In this way, in particular, the colour portions of the light striking the image-recording unit can be evaluated. It is advantageous in this case for this comparison likewise to be carried out in a spatially resolved manner or in terms of pixels. In this way, it is possible for the individual signals of the individual pixel elements of the image-recording unit to be compared with one another in each case. If a plurality of pixel elements which correspond to the imaging of an effect pigment are aggregated in this case, then as a result the pigment-specific properties (preferably averaged) are obtained. In the event that the images or the characteristic intensity values are calculated, these values can be multiplied with one another for example or can be jointly subjected to other mathematical operations such as averaging, summation and the like.

It is preferably possible in this case for images or details of these images to be lined up mathematically, in particular for the purpose of this comparison. In this case both a comparison of all the images (in particular in terms of pixels) can be carried out or, on the other hand, the comparison can relate to individual pixel areas of the image. In this case it is preferable for those pixel areas or pixel ranges which substantially correspond to the imaging of the effect pigments to be selected for the comparison. In order to determine these areas, use can be made of the formation of the threshold values as described above.

On the basis of this comparison, conclusions can be drawn on the colour properties of the surface or of the individual effect pigments (sparkles).

A camera technology would also be possible which is designed in such a way that each pixel registers not only the brightness but also spectral information of the light striking it. In the case of a camera of this type uniform pixels are nevertheless used, unlike colour image cameras. The Applicants thus reserve the right to claim protection.

In a preferred method the surface is a surface provided with a layer of paint. This can be for example, and in a preferred manner, the surfaces of vehicle bodies, but it would also be possible for the surfaces to be surfaces of pieces of furniture, for example of tables or the like.

In a further advantageous method the layer of paint has pigments, for example effect pigments. These effect pigments can be for example, as mentioned above, small metallic particles which are present in the layer. It is advantageous in this case for these effect pigments to have a flop behaviour, i.e. for example a specified change in colour or even a change in intensity, depending upon the angle at which the light strikes the pigments.

In a further advantageous method the irradiation device is designed in such a way that the radiation in the two different wavelengths is irradiated at precisely the same angle onto the surface. In this way, it is advantageous for the radiation in the first wavelength range and the radiation in the second wavelength range to be irradiated onto the surface in a collinear manner with each other.

In a further advantageous method, radiation in a third wavelength range which differs from the first wavelength range and also from the second wavelength range is additionally irradiated onto the surface at the first angle of incidence and the image-recording unit records the radiation reflected and/or scattered by the surface, and in this way it records in turn a third spatially resolved image.

It is advantageous for the recording of this third image also to be carried out in a manner staggered in terms of time from the two other images. In this way, it is possible for example for light of three different colours, for example red, green and blue, to be irradiated onto the surface. In this way, the colours of the individual pigments or the colours at which the pigments reflect light back can also be determined from a comparison of the images. If for example a specific pixel of the image-recording unit displays a high intensity value in the red range at a specific point, the conclusion can be drawn from this that the corresponding sparkle or effect pigment is reflecting back the light in particular of the red wavelength range.

In this way, the colour value of the effect pigments contained in the paint can be represented approximately for example in the mass content for colour, for example the CIELab system.

In a preferred method radiation is irradiated from a plurality of irradiation devices at different angles onto the surface and is then recorded by the image-recording device. Alternatively, it would also be possible for the irradiation device to deliver only one wavelength range and for the wavelengths to be separated on the other side with respect to the detector, for example by different filter elements being pressed in front of the radiation detector device. In this case too, a multiplicity of images are recorded by the black-and-white image camera, but different colour aspects, however, are recorded here, or spatially resolved images at different colour aspects are recorded. In contrast to the variant named above, it is preferable for the two wavelength ranges of the radiation delivered by the irradiation device not to differ in this case, but rather the wavelengths of the radiation striking the image-recording unit.

The Applicants retain the right to claim protection for this procedure accordingly as well. In this case too, the two images are recorded with radiation at the same angle of incidence.

In the case of a further advantageous embodiment radiation is directed onto the surface by a plurality of irradiation devices and at different angles of incidence. In this way, for example, light could be irradiated onto the surface at specific angles, such as 45°, 15° or 60°.

It is advantageous for the radiation to be light and, in a particularly preferred manner, light in the visible wavelength range.

Alternatively, it would also be possible for the light to be irradiated onto the surface from only one direction and to be recorded by a plurality of different detection devices. In this way, in particular, the effect pigments could be illuminated and observed at different angles.

The present invention further relates to an apparatus for investigating optical surface properties. This apparatus has a first irradiation device which directs radiation at a pre-set angle of incidence onto a surface to be investigated. In addition, the apparatus has a radiation detector device which records the radiation irradiated onto the surface by the first irradiation device and reflected back or transmitted from the surface at a detection angle. In this case the radiation detector device has an image-recording unit which records spatially resolved black-and-white images.

According to the invention the irradiation device is designed in such a way that it is suitable for the delivery—staggered at least in part in terms of time—of radiation in at least two different wavelength ranges at the same angle of incidence, and the image-recording unit as far as the recording of a first image which corresponds to the radiation in the first wavelength range and which corresponds to the radiation in the first wavelength range and is suitable for recording a second image.

In this way, it is also proposed in this case that the image-recording unit should record images of radiation in two different wavelengths and that these different wavelengths should be irradiated onto the surface at the same angle of incidence in each case. The corresponding radiation is to be understood in this case as being that radiation which has been irradiated onto the surface by the corresponding irradiation device with the aforesaid first or second wavelength range.

It is advantageous for the irradiation device also to be suitable for the delivery of radiation in a third wavelength range and it is advantageous for the image-recording unit also to be suitable for recording a third spatially resolved image (thus the aforesaid wavelength range).

In the case of a further advantageous embodiment the apparatus has a comparator device which compares at least the first image with the second image. On the basis of this comparison, conclusions can also be drawn in particular on colour characteristics of the surface or the effect pigments respectively.

It is advantageous for the apparatus to have a plurality of irradiation devices which illuminate the surface at different angles. In this case it is advantageous for a plurality of irradiation devices and, in a particularly preferred manner, all the irradiation devices to be suitable for the delivery of light of different wavelength ranges. In this way, these irradiation devices irradiate the light onto the surface at different angles.

In the case of further advantageous embodiments the irradiation device has a first light source which delivers radiation in the first wavelength range and a second light wave which delivers radiation in the second wavelength range as well as an irradiation direction arrangement which has the effect that the radiation in the first wavelength range and the radiation in the second wavelength range are irradiated onto the surface at the same angle of incidence. It is advantageous in this case for the first light source and preferably also the second light source to be light-emitting diodes in each case. In this case these LEDs can direct light in different wavelength ranges onto the surface.

The irradiation direction arrangement has the effect that the radiation in the first light source and of the second light source strike the surface in a substantially collinear manner. Instead of the irradiation direction arrangement it would also be possible for only one light source to be provided and a plurality of filter elements—which can be pressed in front of this light source—therefor. It would also be possible in this way for light of different wavelengths to be projected in a collinear manner onto the surface, in which case, however, the intensity of the radiation striking the surface is weakened by the filter elements in each case.

In the case of a further advantageous embodiment the irradiation direction arrangement has at least one mirror element. This mirror element can be for example a dichroic mirror, which allows light of a specified wavelength to pass and reflects (or absorbs) light of a further wavelength more or less completely. As well as or in addition to the mirror elements, however, use can also be made of other elements, for example diffusion discs, lenses and the like.

In the case of a further advantageous embodiment the apparatus has at least one processor device which establishes information, which is characteristic of a colour of at least one portion of the surface, from a comparison of the recorded images. It is preferable for a property to be established which is characteristic of the sparkles or an optical behaviour of at least one effect pigment and preferably a multiplicity of effect pigments. It is thus advantageous for the processor device to evaluate the respective images in a spatially resolved manner and thus also to carry out a comparison in a spatially resolved manner or individually in each case for the respective pixels of the image-recording unit.

BRIEF DESCRIPTION OF THE DRAWINGS

Further advantageous embodiments are evident from the accompanying drawings. In the drawings

DETAILED DESCRIPTION OF THE DRAWINGS

Figure 1A:
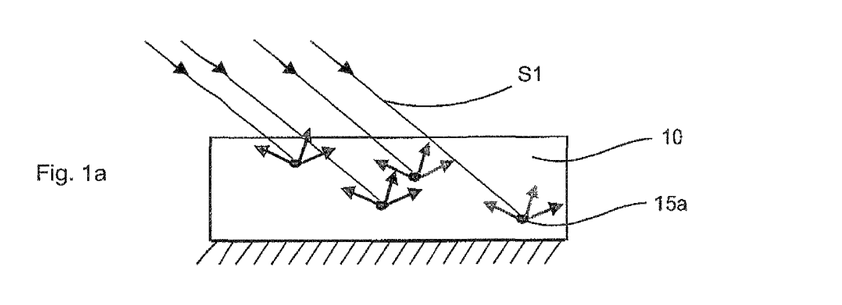
FIGS. 1a-1c are three illustrations to show effect pigments.
Figure 1B:
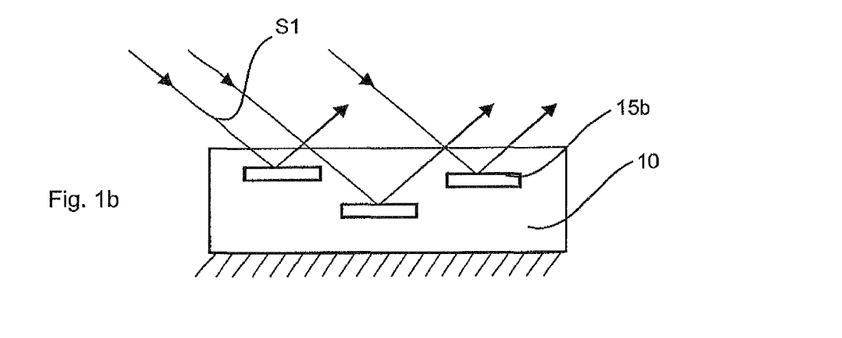
Figure 1C:
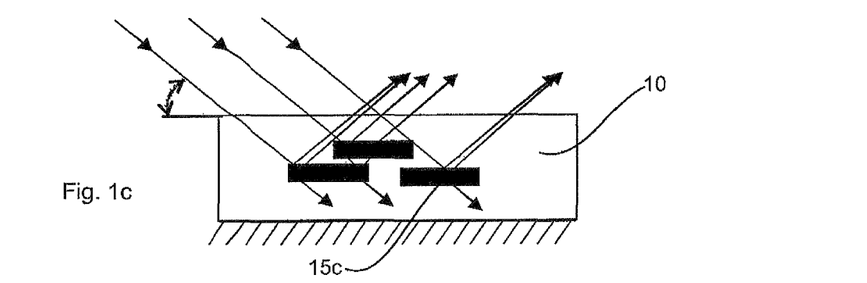

FIGS. 1a to 1c show three examples of pigments. In the case of the design shown in FIG. 1a the surface or the coating respectively has absorbent pigments 15a. These absorbent pigments 15a have a specific colour and the paint colour results in this case from selective absorption and scattering of the light in all directions.

In the illustration shown in FIG. 1b metallic effect pigments 15b are provided in the surface or the coating 10 respectively. These effect pigments produce a metallic shine by a mirroring reflection of the light.

The pigments 15c shown in the example of FIG. 1c are pearlescent pigments which likewise have a specific colour and a pearlescent shine, but, in addition, a change in colour or a colour flop can occur as a result of an interference of the reflected light.

These colour flops can be both a light/dark flop and a colour flop. In this way, the colour impression is also dependent upon the geometry of illumination and observation.

Use is also made of substrates dyed in colour, such as for example glass flakes or flakes based upon $SiO_2$ which reflect the light filtered in a specific direction.

By means of a suitable spectral choice of the illuminating light it is also possible for non-visible phenomena, such as for example the reflex radiation in the heat of the pigments, to be characterized.

Figure 2:
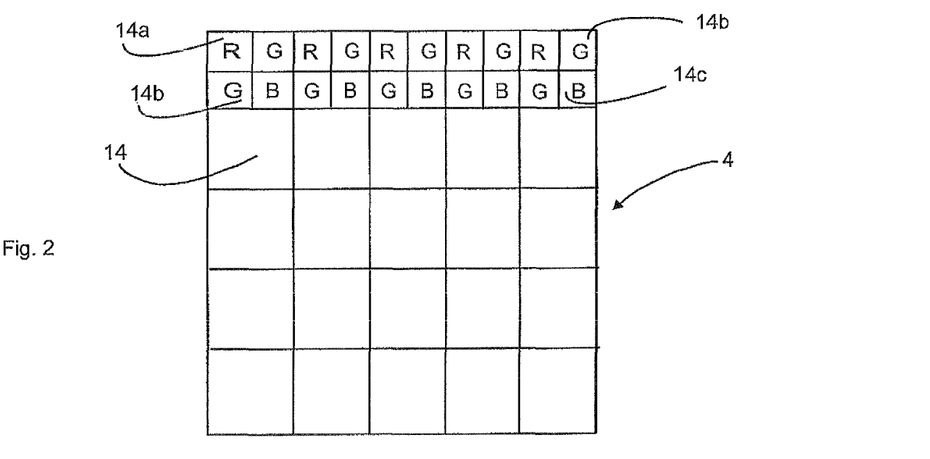
FIG. 2 is an illustration of an image-recording unit for a colour image camera.

FIG. 2 shows an example of an image-recording unit 4a in the form of a colour image camera or a colour image CCD chip. This image-recording unit 4a has in this case a plurality of image-recording elements 14 which in turn are subdivided into individual subsidiary elements 14a, 14b, 14c which are suitable for recording different colours. The subsidiary elements 14a designated R are used to record light in the red colour range, the subsidiary elements 14b designated G are used to record light in the green colour range and the subsidiary elements 14c designated B are used to record light in the blue spectral range. If the light reflected by the effect pigments, for example 15c, now has a predominantly red portion but arrives at the elements 14b or 14c, then they will deliver an incorrect value for the intensity. It is therefore proposed within the scope of the invention that, instead of the image-recording unit 4a shown in FIG. 2, use should be made of an image-recording element which has a plurality of uniform detectors and which can therefore record and deliver only black-and-white images.

Figure 3:
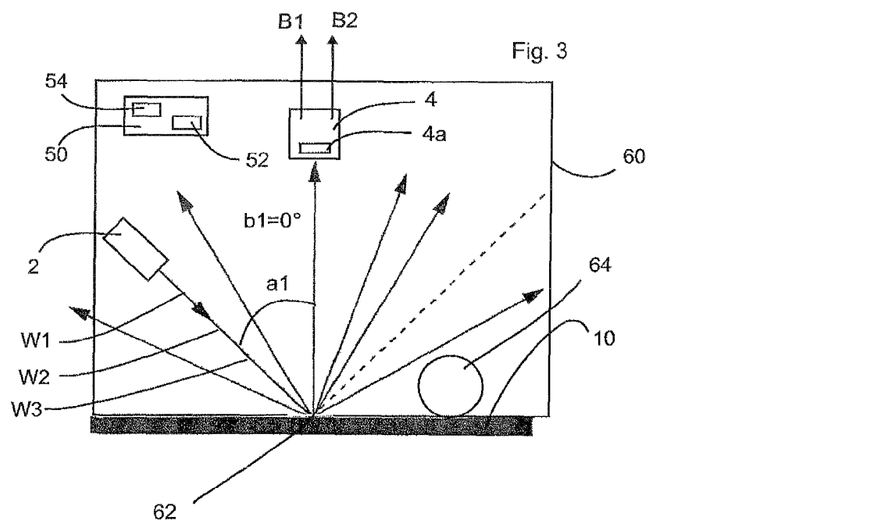
FIG. 3 is a diagrammatic illustration of an apparatus according to the invention.

FIG. 3 accordingly shows a design according to the invention of an apparatus 1 for investigating optical surface properties. In this case light is directed by an irradiation device 2 onto the surface 10 and the light passed on—for example reflected or scattered—by this surface arrives in part at a radiation detector device 4 which has an image-recording unit 4a. This image-recording unit 4a can be suitable in this case for recording spatially resolved images B1, B2, which are black-and-white images in each case, or sets of data characteristic of images of this type respectively.

In this case the irradiation device 2 directs radiation in a first wavelength range W1 and of a second wavelength range W2 onto the surface. This irradiation is carried out staggered in terms of time in this case, as mentioned above. In addition, radiation in the wavelength range W3 can also be irradiated onto the surface. In this way, it would be possible for first green, then red and then blue light to be irradiated in succession onto the surface and for the respective reactions to be delivered in each case as the images B1, B2, B3 by the image-recording unit.

The reference a1 designates the angle of incidence at which the radiation is irradiated by the irradiation device 2 onto the surface 10. This angle is indicated here with respect to a direction at a right angle to the surface. The angle b2, at which the radiation is recorded by the radiation detector device 4, amounts accordingly to 0°, i.e. the radiation is preferably recorded in a direction at a right angle to the surface.

The reference number 50 designates a processor device which is used to evaluate the images recorded by the image-recording unit 4a. The processor device 50 has in this case a comparator device 52 which compares the recorded images with one another. In this way, for example, the intensities can be maintained which were recorded in the different colour ranges (by the black-and-white camera). Conclusions can also be drawn on the colour impression of corresponding effect pigments on the basis of this comparison of the intensities.

The reference number 54 designates a memory device in which are stored the individual images recorded by the image-recording device 4 or the individual figures from which these images are capable of being derived. Position data which are characteristic of a position of the apparatus 1 with respect to the surface can be stored in this memory device. In addition, the apparatus 1 can have an output device in order to show the data, such as for example a display or the like.

The various images or flakes are aligned in a calculating device with the aid of suitable algorithms. As a result, the pixels belonging to a flake are determined from all the images.

It is advantageous for the apparatus according to the invention also to have a position or distance detection device in order to be able to compare two recordings—which were made at different points on the surface 10 with each other also with respect to their distance. In this way, it is possible to measure a complete surface, for example the part of a body of a vehicle, by a multiplicity of recordings. It is possible for both the irradiation device 2 and the radiation detector device 4 to be arranged in one housing 60 and for this housing advantageously to have essentially one opening 62 in a region in which the radiation is to be discharged onto the surface.

In addition, a wheel 64 which is used for moving the apparatus 1 with respect to the surface 10 can be arranged on the housing 60. It is advantageous for this wheel also to be used in this case to determine distances. It would also be possible, however, for the apparatus 1 to be held on a movement element such as for example a robot arm and thus to be moved with respect to the surface 10 to be investigated.

It is advantageous for the images recorded by the image-recording device also to have assigned to them positions of the apparatus with respect to the surface 10, or data which are characteristic of these positions. This assignment is advantageously carried out by means of a processor device.

Figure 4:
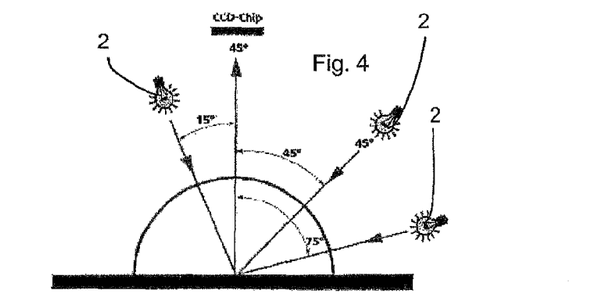
FIG. 4 is a further diagrammatic illustration of an apparatus according to the invention.

FIG. 4 shows a further embodiment of the apparatus according to the invention. In the case of this embodiment a plurality of irradiation devices 2 are provided which irradiate the light at different angles (shown in each case relative to the perpendicular with respect to the surface 10). In this way, the surface is illuminated at the aforesaid different angles and the light in this case is recorded in a direction at a right angle to the surface 10 in each case. Each of these irradiation devices can be designed in this case in the manner shown, i.e. so as to be suitable for the delivery of radiation in different wavelengths staggered in terms of time.

It is advantageous for the apparatus to have at least two irradiation devices of this type, which irradiate the radiation at different angles onto the surface and, in a particularly preferred manner, at least three irradiation devices, which irradiate the radiation at different angles onto the surface 10. It is advantageous for the irradiation directions of a plurality of irradiation devices and for the irradiation direction of the radiation passed on from the surface 10 to the image-recording device 4 to be in one plane. It is also possible, however, for the radiation receiver and the irradiation device not to be in one plane.

Figure 5:
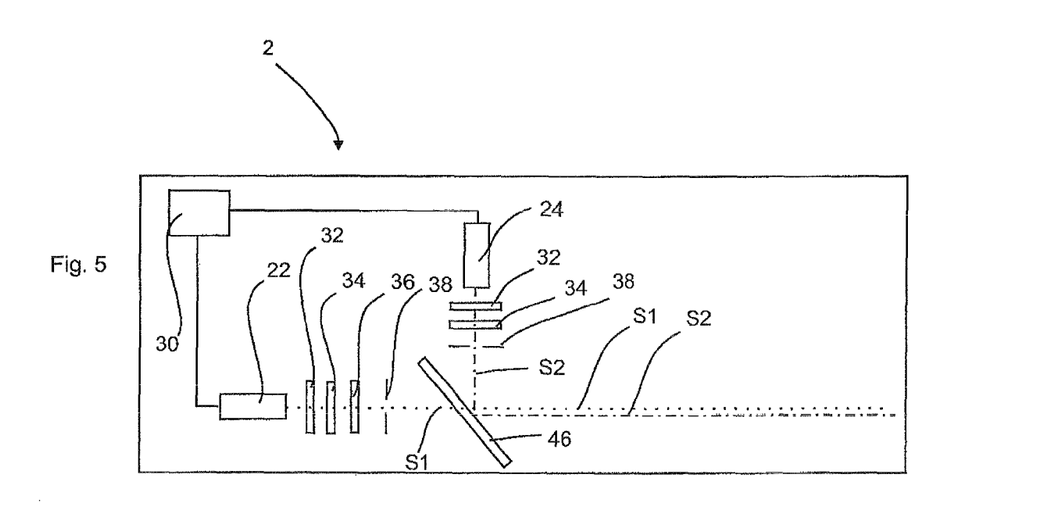
FIG. 5 is an illustration of a first embodiment of an irradiation device.

FIG. 5 is an illustration of an irradiation device 2. This irradiation device has in this case a first radiation or light source 22 and a second radiation or light source 24. The first radiation source 22 irradiates a light beam S1 with a wavelength range W1 which strikes a mirror element 46 which in this case can be a dichroic mirror. In this case the light beam S1 passes through this mirror element 46 on account of its wavelength.

The light source 24 directs a second beam component S2 with a wavelength range W2 likewise onto the mirror element 46. In this case this mirror element 46 is designed in such a way that it reflects the radiation S2 on account of the different wavelength, so that both the radiation S1 and the radiation S2 are discharged out of the irradiation device 2 in a manner collinear with each other. In FIG. 5 the two radiations S1 and S2 have been shown offset from each other in order to clarify the manner of functioning, but in fact the two radiations S1 and S2 are situated one directly on the other.

The reference number 32 relates to an optical element such as for example a diffusion disc which the light arriving from the light source 22 and 24 respectively strikes. The reference number 34 designates a further optical element such as for example a lens device which is used for bundling the radiation S1 and S2 respectively. The reference number 36 can indicate a further optical element such as for example a filter element which allows only a specific portion of the wavelength to emerge. The reference number 38 relates in each case to a screen device which is likewise used for forming a clean light beam S1 and S1 respectively. The sequence of the elements 32, 34, 36, 38 in the direction of the light beams can also be arranged differently depending upon the application.

In addition to the two light sources 22 and 24 it would also be possible for a further light source 26 to be provided which can be arranged for example next to the light source 24 on the right in FIG. 5 and which likewise directs a beam S3 (not shown) vertically downwards onto a further mirror element (not shown). In this case three beams or bundles S1, S2, S3 collinear with one another would be discharged from the irradiation device 2. Optical elements 32, 34, 36, 38 could also be arranged downstream of the mirror elements 46.

Figure 6:
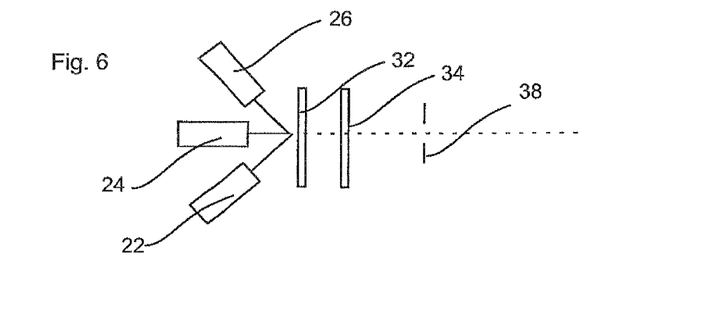
FIG. 6 shows a further embodiment of an irradiation device according to the invention.

FIG. 6 shows a further embodiment of an irradiation device 2. In the case of this embodiment three radiation sources 22, 24, 26 are provided which direct their light onto a diffusion disc 32 in each case. The diffusion disc in this case can be a holographic optical element. In this case the light sources 22, 24, 26 are arranged in such a way that they direct their light onto the same area or the same point respectively of the diffusion disc 32. In order to achieve this, reflective elements, such as for example lenses, cylindrical lenses, perforated screens and the like, can also be arranged between the light sources and the diffusion disc 32.

Further optical elements such as lenses 34 or perforated screens 38 or the like can also be provided along the radiation paths S1, S2, S3.

The reference number 30 both in FIG. 5 and in FIG. 6 relates to a control device which controls the radiation emission through the irradiation device 2. In this case the irradiation device can be controlled in such a way that the individual light sources 22, 24, 26 deliver their light in a manner staggered in terms of time with respect to one another. In addition, depending upon the measurement principle it may be desired for the light sources 22, 24, 26 to deliver their light simultaneously at least for a time, so that as a whole a mixture of light, for example a specific type of a white light, can be created.

Figure 7A:
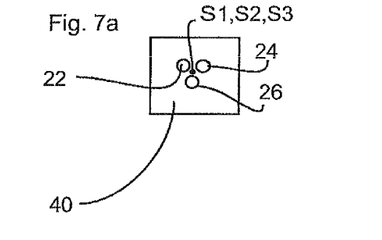
FIGS. 7a, b show a further embodiment of an irradiation device according to the invention.
Figure 7B:
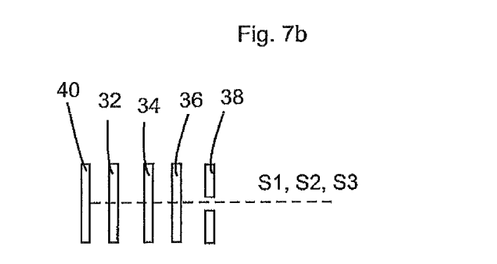

FIGS. 7a, 7b show a further embodiment of an irradiation device 2. In the case of this one embodiment the light sources 22, 24, 26 can be attached for example in the form of LED semiconductor chips to a carrier 40 or a substrate respectively, for example ceramic material. These are then contacted (bonded) in order to make it possible to actuate them individually. Since the semiconductor chips are in part significantly smaller than 0.5 $mm^2$ in their dimensions, they can be positioned very close to one another. In this way, the divergence of the individual chips, which have a different spectral radiation characteristic, from the optical axis of the illumination system is only very slight and it is possible to speak of a collinear illumination (S1, S2, S3). In this case too, diffusion discs 32, screens 38, lenses 34, filters 36, holographic optical elements (not shown) can be incorporated into the beam path.

Figure 8:
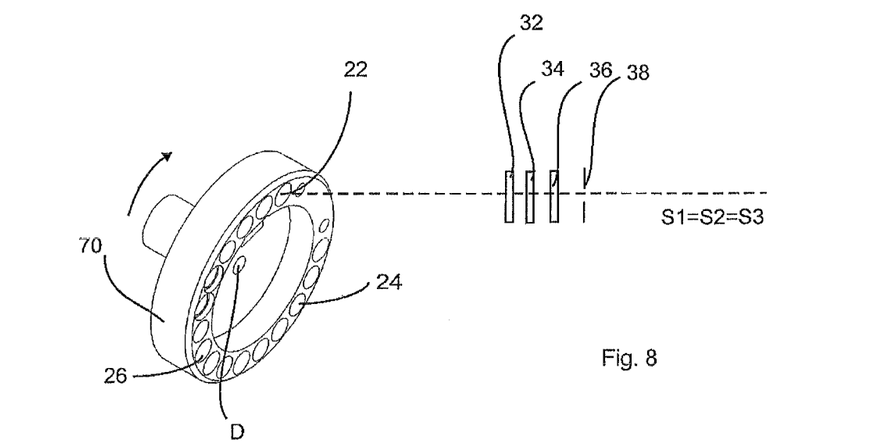
FIG. 8 shows a further embodiment of an irradiation device according to the invention.

FIG. 8 shows a further possibility of carrying out the illumination. In this case a plurality of light sources 22, 24, 26 (for example LEDs) are arranged on a wheel which is rotatable about an axis of rotation D. As soon as an LED is in alignment with the optical axis of the illumination system (S1=S2=S3), it is activated and illuminates the surface by way of various optical components, such as for example diffusion discs 32, screens 38, optical filters 36, lenses 34, filters 36, holographic optical elements. After that, the wheel is turned further until the next LED is in alignment.

During a sequence of the method according to the invention the light of a first wavelength W1 is thus first directed onto the surface and from the surface onto the image-recording unit 4a. After that, light of the wavelength range W2 is irradiated and recorded accordingly. The corresponding images B1 and B2 (or the corresponding figures) are then passed on by the image-recording unit to a processor unit and are compared with each other by the latter. On the basis of this comparison the processor unit 50 can deliver information which is characteristic of the surface and, in particular, also the effect pigments thereof. In particular, information on colour properties of the effect pigments can also be supplied in this case. It is also possible, however, for the image data on each individual wavelength range to be evaluated separately, for example with respect to a maximum intensity of the radiation striking the image-recording unit. In addition, by means of this evaluation it is possible to obtain colour information as to whether the image-recording device used is in fact a black-and-white image camera or a radiation detector device which does not itself supply colour information.

Instead of the embodiments shown in FIG. 5 and FIG. 6 it would also be possible for only one light source 22 to be present which emits for example white light and for the light source 22 and the surface 10 to have provided between them a filter element with variable filters, for example a filter wheel, or a tunable filter which can place different filter elements—which allow different colour portions of the light to reach the surface in each case—in the radiation path. In addition, by means of this apparatus the surface can be illuminated with changing colours in succession.

The apparatus according to the invention and the method according to the invention can be used for quality assurance in conjunction with paints and in particular in the field of motor vehicle repairs, in particular when using effect pigment paints. In detail, a suitable repair paint can be determined with the apparatus according to the invention. In addition, it would also be possible for the apparatus according to the invention to supply data which are used by a matching software program in order to determine the data of a replacement paint.

The Applicants reserve the right to claim all the features disclosed in the application documents as being essential to the invention, insofar as they are novel either individually or in combination as compared with the prior art.

LIST OF REFERENCES 1 apparatus
2 irradiation device
3 radiation detector device
4a image-recording unit
10 surface
14 image-recording elements
14a, 14b, 14c subsidiary elements
15a absorbent pigments
15b metallic colour pigments
15c pearlescent pigments
22, 24, 26 light sources
30 control device
32 optical element (diffusion disc)
34 optical element (lens device)
36 optical element (filter element)
38 screen device
40 carrier
46 mirror element
50 processor device
52 comparator device
54 memory device
60 housing
62 opening
64 wheel
70 wheel
B1, B2, B3 spatially resolved images
R image-recording elements for recording light in the red colour range
G image-recording elements for recording light in the green colour range
B image-recording elements for recording light in the blue colour range
W1, W2, W3 wavelength ranges
S1, S2, S3 light beams
a1 angle of incidence
b1 detection angle
D axis of rotation

The invention claimed is:

1. A method of investigating optical properties of surfaces, wherein the surfaces include a surface provided with a layer of paint, wherein the layer of paint has effect pigments, the method comprising:

irradiating radiation with an irradiation device at a first pre-set angle of incidence with respect to the surface onto the surface to be investigated; and receiving, at a radiation detector device, radiation scattered and/or reflected by the surface, wherein the radiation detector device is arranged at a pre-set detection angle with respect to the surface and has an image-recording unit which records black-and-white images, wherein this radiation detector device permits a spatially resolved detection of the radiation reaching it, wherein the irradiation device directs radiation in a first wavelength range onto the surface and the image-recording unit records a first spatially resolved image of this radiation scattered and/or reflected from the surface and the irradiation device directs radiation in a second wavelength range onto the surface and the image-recording unit records a second spatially resolved image of this radiation scattered and/ or reflected from the surface, wherein the radiation in the first wavelength range and the radiation in the second wavelength range, which differs from the first wavelength range at least in part, are directed staggered at least in part in terms of time onto the surface, and the radiation in the first wavelength range and the radiation in the second wavelength range are irradiated at the same angle of incidence onto the surface, wherein flake characteristics of the first spatially resolved image and the second spatially resolved image are calculated and as a result optical properties of the effect pigments at the respective illumination angle are determined, wherein radiation in a third wavelength range which differs from the first wavelength range and also from the second wavelength range is irradiated onto the surface at the first angle of incidence, and the image-recording unit records the radiation reflected and/or scattered by the surface, and in this way records a third spatially resolved image, wherein the irradiation directions of the irradiation devices and the irradiation direction of the radiation passed on from the surface to the image-recording unit are in one plane, wherein the first, second and third images are compared with each other, and the colours of the individual pigments or the colours at which the pigments reflect light back are determined from the comparison of the first, second and third images, wherein both the irradiation device and the radiation detector device are arranged in one housing, and wherein the housing has one opening in a region in which the radiation is to be discharged onto the surface.

2. The method according to claim 1, wherein the first, second and third images are aligned.

3. The method according to claim 1, wherein the comparison of the entire image is carried out, or in terms of pixels.

4. The method according to claim 1, wherein the comparison relates to individual pixel areas of the image, and wherein the pixel areas correspond substantially to the imaging of the effect pigments.

5. The method according to claim 4, wherein the pixel areas are established at the pixel level or in the histogram by a mathematical formation of a threshold value specified in terms of formulae.

6. The method according to claim 5, wherein the mathematical formation of the threshold value is carried out in a fixed or a dynamic manner, and the formation of the threshold value specified in terms of formulae is derived from the image brightness or image contrast.

7. The method according to claim 1, wherein the effect pigments are represented in an isolated manner by the formation of a threshold value in the overall image and for the characteristic optical properties of these effect pigments reflection behavior and spatial scattering characteristics are determined.

8. An optical surface property investigation apparatus comprising:
a first irradiation device which directs radiation at a first pre-set angle of incidence onto a surface to be investigated, wherein the surface is provided with a layer of paint, wherein the layer of paint has effect pigments; and
a radiation detector device which records the radiation irradiated onto the surface by the first irradiation device and reflected back from the surface at a detection angle, wherein the radiation detector device has an image-recording unit which records spatially resolved black-and-white images, wherein the irradiation device is suitable for the delivery—staggered at least in part in terms of time—of radiation in at least two different wavelength ranges at the same angle of incidence, and the image-recording unit is suitable for recording a first image which corresponds to the radiation in the first wavelength range, and for recording a second image which corresponds to the radiation in the second wavelength range, wherein the apparatus has at least one processor device which calculates flake characteristics of the different images with the different spectral illuminations and as a result, determines the optical properties of the effect pigments at the respective illumination angle, wherein radiation in a third wavelength range which differs from the first wavelength range and also from the second wavelength range is irradiated onto the surface at the first angle of incidence by the first irradiation device, and the image-recording unit records the radiation reflected and/or scattered by the surface, and in this way records a third spatially resolved image, wherein the irradiation directions of the irradiation devices and the irradiation direction of the radiation passed on from the surface to the image-recording unit are in one plane, wherein the first, second and third images are compared with each other, and the colours of the individual pigments or the colours at which the pigments reflect light back are determined from the comparison of the first, second and third images, wherein both the irradiation device and the radiation detector device are arranged in one housing and wherein the housing has one opening in a region in which the radiation is to be discharged onto the surface.

9. The apparatus according to claim 8, wherein the apparatus has a comparator device which compares the first image with the second image.

10. The apparatus according to claim 8, wherein the irradiation device has a first light source which delivers radiation in the first wavelength range and a second light source which delivers radiation in the second wavelength range as well as an irradiation direction arrangement which has the effect that the radiation in the first wavelength range and the radiation in the second wavelength range are irradiated onto the surface at the same angle of incidence.

11. The apparatus according to claim 10, wherein the irradiation direction arrangement has at least one mirror element.

12. The apparatus according to claim 8, wherein the apparatus has at least one processor device which establishes information, which is characteristic of a colour of at least one portion of the surface, from a comparison of the recorded images.

13. The apparatus according to claim 8, wherein the apparatus has exactly one image-recording unit.

14. The apparatus according to claim 8, wherein the radiation detector device records radiation in a direction at a right angle to the surface.

15. The apparatus according to claim 8, wherein the processor device draws conclusions on different colour influences of the effect pigments on a basis of the images with different colour components recorded.

16. The apparatus according to claim 8, wherein a wheel which is used for moving the apparatus with respect to the surface is arranged on the housing, wherein this wheel is also used to determine distances.

17. Use of the apparatus according to claim 8 in the field of motor vehicle repairs, wherein the apparatus determines a suitable repair paint.

18. An optical surface property investigation apparatus comprising:
a first irradiation device and at least a second irradiation device which direct radiation at a pre-set angle of incidence onto a surface to be investigated; and
a radiation detector device which records the radiation irradiated onto the surface by the first and/or the at least second irradiation device and reflected back from the surface at a detection angle,
wherein the radiation detector device has an image-recording unit which records spatially resolved black-and-white images wherein the first and the at least second irradiation device each are designed in such a way that it is in each case suitable for the delivery—staggered at least in part in terms of time—of radiation in at least two different wavelength ranges at the same angle of incident, and the image-recording unit is suitable for recording a first image which corresponds to the radiation in the first wavelength range, and for recording a second image which corresponds to the radiation in the second wavelength range, wherein the first and the second irradiation device irradiate the radiation at different angles onto the surface, wherein the irradiation directions of the irradiation devices and the irradiation direction of the radiation passed on from the surface to the image-recording unit are in one plane, wherein both the irradiation device and the radiation detector device are arranged in one housing, and wherein the housing has one opening in a region in which the radiation is to be discharged onto the surface.

19. The apparatus according to claim 18, wherein the radiation detector device records radiation in a direction at a right angle to the surface.

* * * * *